United States Patent [19]
Kortright et al.

[11] Patent Number: 4,752,563
[45] Date of Patent: Jun. 21, 1988

[54] MONOCLONAL ANTIBODY FOR RECOVERY OF LEUKOCYTES IN HUMAN PERIPHERAL BLOOD AND METHOD OF RECOVERY EMPLOYING SAID MONOCLONAL ANTIBODY

[75] Inventors: Kenneth H. Kortright, Copper City; David E. Hofheinz, Homestead, both of Fla.

[73] Assignee: Coulter Corporation, Hialeah, Fla.

[21] Appl. No.: 799,489

[22] Filed: Nov. 19, 1985

[51] Int. Cl.$^4$ ............... C12Q 1/02; G01N 33/577
[52] U.S. Cl. .................................. 435/2; 435/4; 435/7; 435/29; 435/68; 435/70; 435/172.2; 435/240.27; 436/518; 436/526; 436/528; 436/534; 436/548; 530/387; 935/108
[58] Field of Search .............. 435/2, 7, 29, 4, 68, 435/70, 172.2, 240, 241; 436/548, 518, 526, 528, 534; 935/103, 104, 108, 110; 530/387

[56] References Cited

U.S. PATENT DOCUMENTS 4,429,008  1/1984  Martin ........................ 428/402.2
4,598,051  7/1986  Papahadjopoulos ............ 436/512

OTHER PUBLICATIONS

Robinson, J. et al., Nature, 289:68–71, (1–1981).
Anstee, D. J. et al., Eur. J. Immunology, 12:228–232, (1982).
Barsaum, A. H. et al., Molecular Immunology, 22(4):361–367, (1985).
Rearden, A. et al., Molecular Immunology, 22(4):369–378, (1985).
Langlois, R. G. et al., Journal of Immunology, 134(6):4009–4017, (6–1985).
Bigbee, W. L. et al., Journal of Immunology, 133(6):3149–3155, (12–1984).
Bigbee, W. L. et al., Molecular Immunology, 20(12):1351–1362, (1983).
Liszka, K. et al., Amer. J. Hematology, 15:219–226, (1983).
Ridgewell, K. et al., Biochem. Journal, 209:273–276, (1983).
Ochiai, Y. et al., J. of Immunology, 131:864–868, (8–1983).
Bragman, K. S. et al., Biochem. Biophys. Aeta, 730:187–195, (1983).

Primary Examiner—Margaret Moskowitz
Attorney, Agent, or Firm—Myron C. Cass

[57] ABSTRACT

A murine monoclonal antibody which selectively binds to the determinant site or specific epitope of glycophorin A exposed on the membrane of the erythrocyte and does not bind to other glycophorins. The monoclonal antibody is coated on a microsphere or substrate of a suitable monodispersed variety and utilized in a separation procedure for recovery of white blood cell subsets without lysing of erythrocytes. The bound microspheres are recovered without adverse depletion of the white blood cell population of the sample. The microsphere or bead-to-cell ratio employed is most acceptable for commercial applications of the invention. The invention thus enables accurate assaying of white blood cell subsets in circulating peripheral blood without resorting to lysing of erythrocytes.

8 Claims, No Drawings

4,752,563

MONOCLONAL ANTIBODY FOR RECOVERY OF LEUKOCYTES IN HUMAN PERIPHERAL BLOOD AND METHOD OF RECOVERY EMPLOYING SAID MONOCLONAL ANTIBODY

BACKGROUND OF THE INVENTION

This invention relates to a murine monoclonal antibody particularly useful for assaying of white blood cell subsets in circulating peripheral blood without lysing of erythrocytes. Ancillary objects of the invention include providing improved assay methodology employing said monoclonal antibody for recovery of the white blood cells from a human blood sample utilizing suitable monodispersed microspheres coated with said monoclonal antibody.

PRIOR ART

The employment generally of supports or microspheres coated with monoclonal antibody specific for an antigenic determinant of a cell or tissue for detection and diagnostic applications is well documented in the prior art.

The employment of magnetic particles or microspheres coated with an antibody for sorting and separating a selected cell population from a heterogenous cell population is well known also. U.S. Pat. Nos. 4,230,685, Senyei et al.; 3,970,518, 4,018,886 and 4,115,535, Graver, 4,177,253, Davis, 4,452,773, Molday, 4,454,234 Gerlinski, and 4,267,234, Rembaum, are only some examples of this technology. U.S. Pat. Nos. 4,272,510 Smith et al. and 4,141,687 Forrest et al. teach apparatus suitable for assay purposes using magnetic particles. Use of magnetic microspheres for cell separation is also described in published international patent applications filed by Sintef of Oslo, Norway under the Patent Cooperation Treaty as PCT Application No. 83/00014 filed Apr. 22, 1983, International Publication No. WO83/03920, published Nov. 10, 1983 and PCT Application No. 83/00016 filed Apr. 27, 1983, International Publication No. WO84/02031, published May 24, 1984. Applicants, however, are not aware of successfully accurate use of monoclonal antibody for separating white blood cell subsets from a human peripheral blood sample.

Circulating human blood consists of cellular and liquid components. The cellular components include erythrocytes (red blood cells), platelets and leukocytes (white blood cells). One microliter of a normal whole blood sample includes $5 \times 10^6$ erythrocytes, $3 \times 10^5$ platelets and $5 \times 10^3$ leukocytes. The white blood cell population subdivides into five subsets or populations called Neutrophiles, Eosinophiles, Basophiles, Monocytes and Lymphocytes. In a human having a white blood cell count of $5 \times 10^3$, the blood sample has 3,075 Neutrophiles, 150 Eosinophiles, 25 Basophiles, 250 Monocytes and 1500 Lymphocytes per microliter of blood. The lymphocytes are composed of eight different types with an indication of the presence of several additional functional categories. The majority of cells which control and provide for manufacture of antibodies in the human body are known to be found in that single population of leukocytes called lymphocytes. Further, lymphocyte subsets have been identified as being substantial in number.

It will be readily appreciated that an incisive assay of the leukocyte population of a blood sample is a valuable diagnostic tool. The conventional methods for obtaining such information include automated electronic white blood cell differential instruments, mechanical, electronic and light scattering cell counting techniques. The use of such expensive instrumentation is somewhat of an economic deterent. Further, such methods cannot be employed to make a leukocyte subset determination without specific monoclonal antibodies and special technology. This applies also to use of fluorescent-type technologies. Also some prior art techniques require initial lysing of the red blood cells.

It also is known that the red blood cell (erythrocyte) lacks most cellular organelles and therefore, has only a single membrane, the plasma membrane. Nearly all of the cytoplasmic contents of the cell can be released by osmotic hemolysis to provide "ghosts", which are quite pure plasma membranes. It is determined by known staining techniques that the red-blood cell membrane has several proteins which are rich in carbohydrates. Further, it has been determined that these are cell surface proteins.

The erythrocyte contains a transmembrane protein identified as glycophorin A which consists of sixteen oligosaccharide units attached to a single polypeptide. About 60% of the mass of this glycoprotein is a carbohydrate and these carbohydrate units are located on the outer surface of the cell membrane. The abundance of carbohydrate in glycophorin A enables excellent staining thereof. Proteolytic, chemical modification and electronmicroscopic studies show that glycophorin A has (1) an amino-terminal region containing all of the carbohydrate units, the region being located on the outer surface of the membrane, (2) a hydrophobic middle region which is buried in the hydrocarbon core of the membrane and (3) a carboxyl-terminal region located in the cell and comprising the poly-peptide chain. The carbohydrate units in the amino-terminal portions of the molecule are rich in negatively charged sialic acid groups.

Glycophorin B, also called glycoprotein delta, is the glycoprotein associated with the Ss alloantigens. The presence of methionine or threonine at position 29 defines this alloantigenic difference. Only the amino terminal portion of glycophorin B appears to have been sequenced to date. Glycophorin C refers to the minor constituents called glycoproteins beta and gamma.

The glycoprotein chains that make up the red cell glycophorins can occur as homo- and hetero-dimers with characteristic band patterns following PAGE. Also, it should be noted that differences in the type and degree of glycosylation and sialation further delineate the glycophorins.

Applicants have developed a monoclonal antibody to a specific epitope, a unique binding site, on glycophorin A only. Attempts were made to coat commerically available magnetic microspheres with the anti-glycophorin A monoclonal antibody in a magnetic separation procedure to recover leukocytes from a human whole blood sample. In one case study, Protein A magnetic microspheres available from Molecular Biosystems, of San Diego, Calif., Catalog No. MM002 were used. These particles were polydispersed with average size of from 015 to 2.0 microns as disclosed in U.S. Pat. No. 4,230,685 and a surfactant was found to be necessary. The bead to cell ratio required for a desirable incubation period and percentage of erythrocyte depletion demonstrated impractical commercial utility. Further, adverse interference with leukocyte cell recovery was encountered.

Magnetic microspheres obtained from Duke Scientific of Philadelphia, Pa., Catalog No. 9420A, were utilized in a test study. Here, the particles were polydispered also, i.e., from 0.2 to 0.9 microns and also required surfactant. Agglutination or clumping of the particles was seen. White blood cell recovery was not adequate since loss of leukocytes resulted along with erythrocyte depletion in the process.

Applicant's previous attempts to utilize such commercially available polydispersed magnetic microspheres or beads for separating and recovering leukocytes from a human whole blood sample dissuaded against commercially employing such magnetic particle separation procedures. Bulk manufacturing requirement of the referenced prior conventional magnetic microspheres made it impractical to commercialize this technique utilizing this particle base. However, applicant's have now been able to make improvements in this methodology which gave rise to unexpected and surprisingly successful results. Also, applicant's have determined what kind of magnetic microspheres can be used successfully with their unique monoclonal antibody.

SUMMARY OF INVENTION

The invention embodies a murine monoclonal antibody developed by applicants which binds selectively to a determinant site of glycophorin A exposed on the surface membrane of human erythrocytes. This monoclonal antibody is designated "KC-16". The specificity of binding to anti-glycophorin A enables the KC-16 monoclonal antibody to be utilized in a commercially feasible assay of leukocyte populations in human peripheral blood by a procedure of separation of erythrocytes from the blood without requiring lysing thereof. Further, the separation is achieved without altering morphology of the leukocytes and without adverse depletion of the leukocyte population of the blood sample tested.

One particularly successful assaying procedure involved coating of the KC-16 monoclonal antibody on monodispersed magnetic microspheres or beads having a 1.0 and 4.5 micron size respectively. In each instance, the human blood sample was placed in a test tube with the incubation conducted at room temperature over a time course. A microsphere-to-red blood cell ratio of seven-to-one (7:1) in one instance and 14:1 in another instance was introduced to the test vessel. The microsphere-bound erythrocytes were separated from the blood sample by application of a magnetic force at the bottom end of the test vessel and the remaining sample supernatant decanted and analyzed by light scattering techniques using a cell sorting instrument of Coulter Corporation of Hialeah, Fla. available under the registered trademark EPICS ®.

Red blood cell depletion with attendant white blood cell recovery was successful. Percentage of red blood cell depletion was in the range of 99.5 to 99.99 percent with white blood cell population remaining in the range of 97-98 percent. These results were realized in incubation periods of 5 to 30 minutes. The magnetic microspheres used were selected to exhibit a non-porous polymeric surface and which was surfactant free. They were spherical, monodispersed in character and had a desired uniform concentration of magnetic material.

The KC-16 monoclonal antibody also can be conjugated to non-magnetic microspheres having suitable characteristics for separation of erythrocytes from a peripheral human blood sample and thereafter assaying for leukocyte populations using electronic blood cell counting and sizing techniques performed in a COULTER COUNTER ® type instrument marketed by Coulter Electronics, Inc. of Hialeah, Fla., a wholly owned subsidiary of the assignee of this patent application. The unique specificity of the KC-16 monoclonal antibody enables commercially feasible assay techniques to be employed with available in vitro diagnostic instrumentation.

DESCRIPTION OF THE SPECIFIC EMBODIMENTS

The present invention provides murine monoclonal antibodies, which selectively bind to a specific epitope of glycophorin A exposed on the surface membrane of human erythrocytes. All monoclonal antibodies having this specificity for glycophorin A can be referred to as "KC-16".

An embodiment of a hybrid cell or hybridoma capable of producing KC-16 monoclonal antibodies was prepared as follows: The hybridoma was developed from a fusion of the mouse plasmacytoma cell line, Sp2/0-Ag 14 and splenocytes from a Balb/c mouse injected with whole cells from a fresh human lung adenocarcinoma biopsy. The mouse was injected on three separate occasions at two week intervals and sacrificed four days after the final injection. Cell fusion was carried out according to the procedure developed by Kohler and Milstein (Nature 256:495–497, 1975).

In this fusion, $7 \times 10^7$ splenocytes were fused in 30 percent polyethylene glycol (PEG) and Dulbecco Modified Eagles' Medium (DMEM) with $3.6 \times 10^7$ myeloma cells. After cell fusion, cells were distributed in approximately 1000 cells and cultured in selective media (HAT) containing hypoxanthane, aminopterin and thymidine. The wells were observed regularly under an inverted microscope for cell growth and supernatants from wells showing growth were subsequently harvested and initially screened using an Elisa technique for the production of mouse immunoglobulin. Supernatants from those colonies positive for mouse immunoglobulin were then screened using an indirect immunoperoxidase staining protocol, employing both frozen and paraffin embedded tissue sections of lung adenocarcinoma and normal lung.

The supernatant containing the KC-16 colony demonstrated specific reactivity with erythrocytes and showed no staining of other tissue elements. This colony was recloned twice in soft agarose to ensure that a single clone, KC-16, was obtained. The KC-16 antibody produced by the clones was determined by double immunodiffusion to be a mouse immunoglobulin IgG1. Additional screening was performed utilizing hemagglutination of human erythrocytes types O-negative, O-positive, A-positive, A-negative, B-positive, B-negative, AB-positive and AB-negative blood types.

A sample of the hybrid cell line capable of producing KC-16 monoclonal antibody is on deposit with the American Type Culture Collection 12301 Parklawn Drive, Rockville, Md., 20852 and is assigned the No. CRL 8994.

KC-16 monoclonal antibody also was obtained by affinity purification of ascites fluid from the immunized mouse using the following procedure. Frozen ascites fluid was thawed in a water bath at 37° C. and clots were removed. Heparin was added to the thawed ascites fluid to a final concentration of 2 mg/ml of ascites fluid and mixed for thirty minutes at 25° C. Magnesium chloride solution (1.5M) was then added to a concentration of 0.0344 ml per ml of ascites fluid and mixed for thirty minutes at 25° C. The resultant fluid was ultracentrifuged at $10^5$ G for thirty minutes at 15° C. to provide a supernatant which was separated and then diluted on a 1:1 volume basis with a binding buffer having a pH 9.0 and comprising 1M glycine and 4M sodium chloride. An affinity column was prepared with supported Protein A-Sephorose which was equilibrated with the binding buffer. The buffered supernatant was introduced to the column in a ratio of 1 ml of supernatant to ½ ml of Protein A-Sephorose at 3 × CSA. The column was washed to its baseline with the binding buffer, and the KC-16 antibody was eluted with 0.1M potassium acetate (pH 6.0) as the first peak from the column. The eluted KC-16 antibody was concentrated and diafiltered into PBS with 0.1% azide.

Due to the binding selectivity of the KC-16 monoclonal antibody to a specific glycophorin A epitope exposed on the surface membrane of the erythrocytes, without binding to leukocytes, a separation of the erythrocyte and leukocyte populations from a human whole blood sample can be achieved. In one method of achieving such blood cell separation, the KC-16 monoclonal antibodies can be coated on suitable magnetic microspheres which can then be introduced into a whole blood sample; by means of the KC-16 monoclonal antibodies, the microspheres are selectively bound to the erythrocytes which can be separated from the leukocytes by applying a magnetic field to the microsphere-blood mixture. The resulting separation is achieved without lysing the erythrocytes and without altering the morphology of the leukocytes which are in condition for further assay and analysis and without adverse depletion of white blood cells by reason of clumping or otherwise.

EXAMPLES

Non-porous magnetic microspheres (sometimes called "beads") of generally monodispersed or uniform 4.5 and 1.0 respectively micron diameter were conditioned for binding of KC-16 monoclonal antibodies thereon by pre-coating the microspheres (beads) with rabbit or goat anti-mouse immunoglobulin (RAM or GAM) as follows: 250mg of beads where dispersed in 3ml of distilled water and sonicated for 2–3 minutes. The mixture of beads in water was cooled for several hours at 4° C. The beads were then magnetically separated and the water discarded. The beads were then resuspended in 5 mg of RAM and diluted with 500 microliters of phosphate-buffered saline (PBS); this mixture was incubated at room temperature and mixed end-over-end 4–5 hours. Thereafter the beads were washed 6 times with 4ml portions of the mixture of PBS-1% BSA. The beads were then resuspended in 4ml of PBS-1% BSA and mixed end-over-end, changing the PBS-1% BSA 3 times over 24 hours.

A $5 \times 10^8$ quantity of the suspended beads were pipetted into a siliconized test tube. The beads were magnetically separated from the liquid which was discarded. The beads were then resuspended in PBS and KC-16 monoclonal antibodies were added to the solution to a final concentration of 0.5 mg/ml of solution; the solution was then incubated at room temperature for one hour with mixing. The beads were then washed 6 times with PBS-1% BSA and resuspended in 1 ml of PBS-1% BSA.

Whole blood separation of erythrocytes (RBCs) and leukocytes (WBCs) using the KC-16 coated magnetic microspheres was carried out by mixing the microspheres with a series of whole blood samples ranging from 10–100 microliters to prepare mixtures with microspheres: erythrocyte ratio ranging from 7:1 to 20:1. The mixtures of microspheres and whole blood were incubated in respective test tubes at room temperatures over a period of two minutes with gentle mixing. The test tubes were placed in a magnetic field to separate the erythrocyte-bound magnetic microspheres at the bottom of the test tube, and the leukocytes were decanted with the supernatants which were analyzed by light scattering techniques using a cell sorting instrument of Coulter Corporation of Hialeah, Fla. available under the registered trademark EPICS®. The results of these separations are presented in TABLE I, which indicates that a microsphere to-erythrocyte or cell ratio between 10:1 and 20:1 enables 99.99% depletion of the erythrocytes in a whole blood sample.

TABLE I

| | RATIO OF MICROSPHERES TO RBCs | |
|---|---|---|
| RATIO | % RBCs DEPLETED | % WBCs REMAINING |
| 7:1 | 99.21 | 90 |
| 10:1 | 99.99 | 73.6 |
| 14:1 | 99.99 | 61.2 |
| 20:1 | 99.99 | 78.4 |

In a second series of separations, seven whole blood samples from six different donors were mixed with the KC-16 coated microspheres at the same microsphere-to-cell ratio of 14:1 in each mixture. After one minute, a first supernatant was decanted and after a second period of one minute a second supernatant was decanted; the percentage of erythrocyte depletion and the percentage of leukocytes remaining in both of the two consecutive supernatants were determined using the EPICS® instrument and are shown in TABLE II. TABLE II indicates that an average of 99.97+0.02% of the erythrocytes were depleted after the two consecutive one minute incubations.

TABLE II

| RBC DEPLETION USING KC-16 LABELLED 4.5 MICRON MAGNETIC MICROSPHERES WITH TWO CONSECUTIVE ONE MINUTE INCUBATIONS AT 14:1 RATIO OF MICROSPHERES RBCs | | | |
|---|---|---|---|
| FIRST SUPERNATANT | | SECOND SUPERNATANT | |
| % RBC's DEPLETED | % WBCs REMAINING | % RBCs DEPLETED | % WBCs |
| 99.79 | 78.6 | 99.95 | 71.4 |
| 99.95 | 96.6 | 99.98 | 90.9 |
| 99.94 | 100 | 99.99 | 100 |
| 99.80 | 100 | 99.94 | 100 |
| 99.85 | 100 | 99.95 | 100 |
| 99.94 | 100 | 99.99 | 94.8 |
| 99.97 | 100 | 99.98 | 94.8 |
| 99.89 + .08 | 96.5 + 8.0 | 99.97 + .02 | 93. + 10.0 |

The magnetic microspheres determined to be useful and employed by applicants came from two sources. One example of bead employed is described in the patent applications of Sintef identified hereinabove. Another example of bead employed is marketed by Duke Scientific of Philadelphia, Pa. and identified as 1.0 micron latex-acrylamide.

We believe that the unique specificity of the KC-16 monoclonal antibody adapts it for use with other supports or beads which are non-magnetic in character. In this application, the KC-16 monoclonal antibody is coated on a support or bead of polymeric character, a suitable synthetic plastic which is of a uniform size. After effecting binding of erythrocytes to the KC-16 coated support, separation can be produced by passing the supernatant of the blood sample through a wire mesh of desired gauge which will capture the beads, yet permit passage of the supernatant. Assay for white blood cells then can be performed.

It is known that glycophorin A is the major sialated glycoprotein constituent of the erythrocyte membrane. We believe that the epitope or antigenic site of th glycoprotein A molecule is a specific carbohydrate moiety to which our KC-16 monoclonal antibody selectively binds with the satisfactory results achieved as hereinabove described.

Modifications obvious to one skilled in the art may occur to skilled persons in this field without departing from the scope of inventions.

We claim:

1. A method of assaying the leukocyte population in a human peripheral blood sample without lysing the erythrocyte population of the sample comprising:
   (a) introducing to a contained sample of said blood in a predetermined microsphere-to-cell ratio a quantity of substantially mono-dispersed microspheres coated with a monoclonal antibody produced by the hybrid cell line having the characteristics of the American Type Culture Collection deposit No. CRL 8994;
   (b) bringing the coated microspheres in contact with said blood sample over a sufficient period of time for achieving binding of substantially all of the erythrocytes to the monoclonal antibody coating without adverse depletion of the leukocyte population;
   (c) separating the antibody-bound microspheres from the remaining blood sample; and
   (d) assaying the leukocyte population of the recovered blood sample.

2. The method of claim 1 in which the microspheres are magnetic and separtion of the antibody-bound microspheres from the remaining blood sample is by means of a magnetic field brought into proximity with said microspheres from externally of the container to form an agglutinate.

3. The method of claim 1 in which the microspheres are non-magnetic polymeric supports and separation of the antibody-bound microspheres from the remaining blood sample is by means of a mechanical mesh or screen sized to capture said microspheres upon decanting the sample.

4. The method of claim 2 in which said micropheres are of substantially uniform 4.5 microns in diameter.

5. The method of claim 2 in which ratio of microspheres to erythrocytes introduced to the blood sample is within the range of 7:1 to 20:1.

6. The method of claim 5 wherein said ratio is approximately 14:1.

7. The method of claim 5 in which said ratio is approximately 7:1.

8. The method of claim 2 in which said microspheres are of subtantially uniform 1.0 micron in diameter.

* * * * *